United States Patent
Hingwe et al.

(10) Patent No.: US 11,311,347 B2
(45) Date of Patent: Apr. 26, 2022

(54) TELEOPERATED SURGICAL SYSTEM WITH SURGICAL INSTRUMENT WEAR TRACKING

(71) Applicant: Intuitive Surgical Operations, Inc., Sunnyvale, CA (US)

(72) Inventors: Pushkar Hingwe, Fremont, CA (US); Amy E. Kerdok, San Jose, CA (US); William C. Nowlin, Los Altos Hills, CA (US); David W. Robinson, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 156 days.

(21) Appl. No.: 16/349,208

(22) PCT Filed: Nov. 10, 2017

(86) PCT No.: PCT/US2017/061139
§ 371 (c)(1),
(2) Date: May 10, 2019

(87) PCT Pub. No.: WO2018/089819
PCT Pub. Date: May 17, 2018

(65) Prior Publication Data
US 2020/0214776 A1    Jul. 9, 2020

Related U.S. Application Data

(60) Provisional application No. 62/421,083, filed on Nov. 11, 2016.

(51) Int. Cl.
*A61B 34/35*     (2016.01)
*A61B 34/00*     (2016.01)
(Continued)

(52) U.S. Cl.
CPC .............. *A61B 34/35* (2016.02); *A61B 34/70* (2016.02); *A61B 90/98* (2016.02); *A61B 2034/2051* (2016.02); *A61B 2090/0803* (2016.02)

(58) Field of Classification Search
CPC ......... A61B 34/35; A61B 34/70; A61B 90/98; A61B 2034/2051; A61B 2090/0803; A61B 90/90; A61B 34/20
See application file for complete search history.

(56) References Cited

U.S. PATENT DOCUMENTS 9,247,996 B1    2/2016  Merana et al.
2003/0093103 A1*  5/2003  Malackowski .... A61B 17/1626
                                                     606/170
(Continued)

FOREIGN PATENT DOCUMENTS

CN    105411636 A    3/2016
JP    2004537367 A   12/2004
(Continued)

OTHER PUBLICATIONS

Extended European Search Report for Application No. EP17869266.1 dated Jun. 22, 2020, 11 pages.
(Continued)

*Primary Examiner* — Richard G Louis
(74) *Attorney, Agent, or Firm* — Schwegman Lundberg & Woessner, P.A.

(57) ABSTRACT

A surgical method is provided, comprising: providing an information structure in a computer readable storage device that associates an indication of surgeon skill level in at least one surgical activity performed using the surgical instrument with a surgical instrument actuator safety state of the surgical instrument for use during performance of the at least one surgical activity using the surgical instrument by a surgeon having the indicated skill level; tracking surgical
(Continued)

instrument actuator state of a surgical instrument during performance of a surgical procedure by a surgeon; and transitioning the surgical instrument actuator state of the surgical instrument to the surgical instrument safety state during performance of the at least one surgical activity by the surgeon using the surgical instrument.

10 Claims, 12 Drawing Sheets

(51) Int. Cl.
*A61B 90/98* (2016.01)
*A61B 34/20* (2016.01)
*A61B 90/00* (2016.01)

(56) References Cited

U.S. PATENT DOCUMENTS

| | | | |
|---|---|---|---|
| 2006/0119481 A1* | 6/2006 | Tethrake | A61B 90/98 340/572.1 |
| 2006/0129140 A1* | 6/2006 | Todd | G06K 17/00 606/1 |
| 2008/0211634 A1 | 9/2008 | Hopkins et al. | |
| 2008/0262654 A1 | 10/2008 | Omori et al. | |
| 2013/0193188 A1 | 8/2013 | Shelton, IV et al. | |
| 2014/0276950 A1 | 9/2014 | Smaby et al. | |
| 2014/0358130 A1 | 12/2014 | Gardner | |
| 2015/0289925 A1 | 10/2015 | Voegele et al. | |
| 2016/0249917 A1 | 9/2016 | Beckman et al. | |

FOREIGN PATENT DOCUMENTS

| | | |
|---|---|---|
| WO | WO-03013372 A2 | 2/2003 |
| WO | WO-2019008126 A1 | 1/2010 |
| WO | WO-2015142780 A1 | 9/2015 |

OTHER PUBLICATIONS

International Preliminary Report on Patentability for Application No. PCT/US2017/061139, dated May 23, 2019, 8 pages.

International Search Report and Written Opinion for Application No. PCT/US2017/061139, dated Feb. 19, 2018, 11 pages.

Vertut, Jean and Phillpe Coiffet, Robot Technology: Teleoperation and Robotics Evolution and Development, English translation, Prentice Hall, Inc., Inglewood Cliffs, NJ, USA 1986, vol. 3A, 332 pages.

* cited by examiner

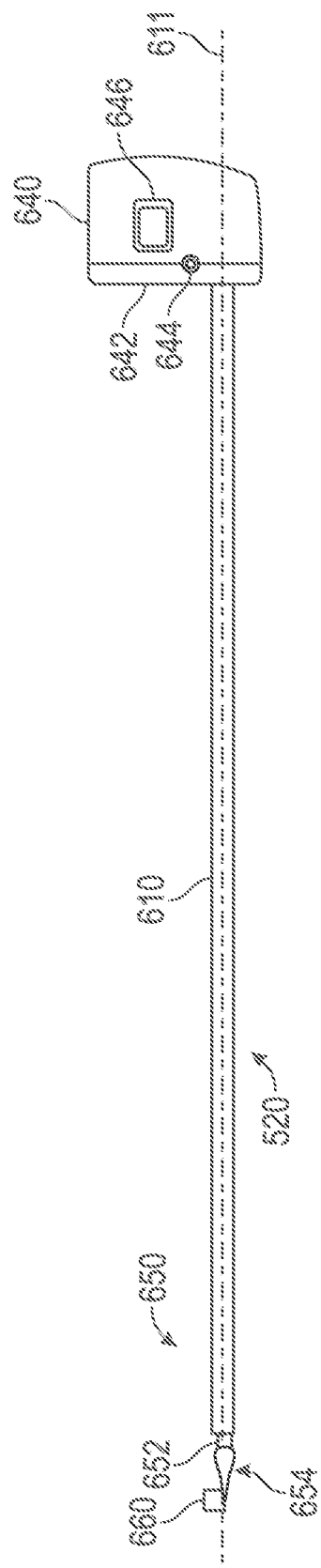
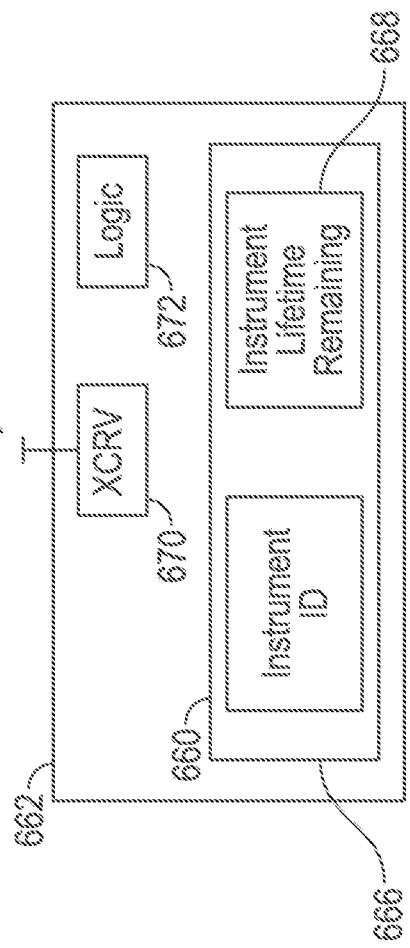
FIG. 6A
FIG. 6B

| Time Stamp | Video Segment | Actuator State |
|---|---|---|
| $t_1$ | Video Image 1 | Actuator State 1 |
| $t_2$ | Video Image 2 | Actuator State 2 |
| ⋮ | ⋮ | ⋮ |
| $t_n$ | Video Image n | Actuator State n |

TELEOPERATED SURGICAL SYSTEM WITH SURGICAL INSTRUMENT WEAR TRACKING

CLAIM OF PRIORITY

This application is a U.S. National Stage Filing under 35 U.S.C. 371 from International Application No. PCT/US2017/061139, filed on Nov. 10, 2017, and published as WO 2018/089819 A1 on May 17, 2018, which claims the benefit of priority to U.S. Patent Application No. 62/421,083, filed on Nov. 11, 2016, each of which is hereby incorporated by reference herein in its entirety.

COPYRIGHT NOTICE

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

BACKGROUND

1. Field of Invention

Inventive aspects are associated with medical devices used during surgery. More specifically, aspects are associated with surgical instrument wear tracking.

2. Art

Surgeons typically undertake extensive study before performing a surgical procedure. Traditionally, surgeons were limited to the study of generic anatomical models, such as photographs or drawings. More recently, various pre-operative diagnostic procedures (e.g., x-ray, CT. MRI, etc.) have made patient-specific anatomical information available.

In some cases, it is desirable to make additional, relevant anatomic and surgical procedure information available to a surgeon. In one aspect, it is desirable to provide a surgeon planning an operation on a particular patient with a surgical site video recording of an earlier surgical procedure performed on the particular patient. In another aspect, it is desirable to provide a surgeon with one or more surgical video recordings of surgical procedures on other patients that are similar to the surgical procedure planned for a particular patient. In one aspect, it is desirable to provide such information to a surgeon prior to the surgeon undertaking a particular surgical procedure. And in another aspect, it may be desirable to provide this information to a surgeon intraoperatively.

In one aspect, it is desirable to configure a video database that includes intraoperative surgical site video recordings of various procedures undergone by various patients. In one aspect, it is desirable to configure a medical device capable of video recording to further include an input that enables a surgeon using the medical device to highlight and annotate the video recording in real time as it is being recorded. In one aspect, it is desirable to configure a computer-based pattern matching algorithm to search through the individual records of the video database, identify relevant video records, and provide a surgeon with this relevant information for a particular surgical procedure.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

A surgical method for use with a teleoperated surgical system that includes a surgical instrument and a surgical instrument actuator. A first information structure is provided in a computer readable storage device that associates a surgical instrument identifier with an indication of remaining useful lifetime of the identified surgical instrument. A second information structure is provided in a second information structure in a computer readable storage device that associates a surgical instrument wear-down actuation state with a surgical instrument lifetime reduction amount. Surgical instrument actuator state of the identified surgical instrument is tracked during performance of a surgical procedure. The indication in the first information structure of remaining useful lifetime of the identified surgical instrument is reduced by the surgical instrument lifetime reduction amount in the second information structure in response to the tracked surgical instrument actuator state matching the surgical instrument wear-down actuation state during the performance of the surgical procedure.

BRIEF DESCRIPTION OF THE DRAWINGS

FIG. 6A is an elevation view of a surgical instrument.

FIG. 6B is an illustrative drawing representing an RFID tracking device associated with an instrument in accordance with some embodiments.

DETAILED DESCRIPTION

Figure 1:
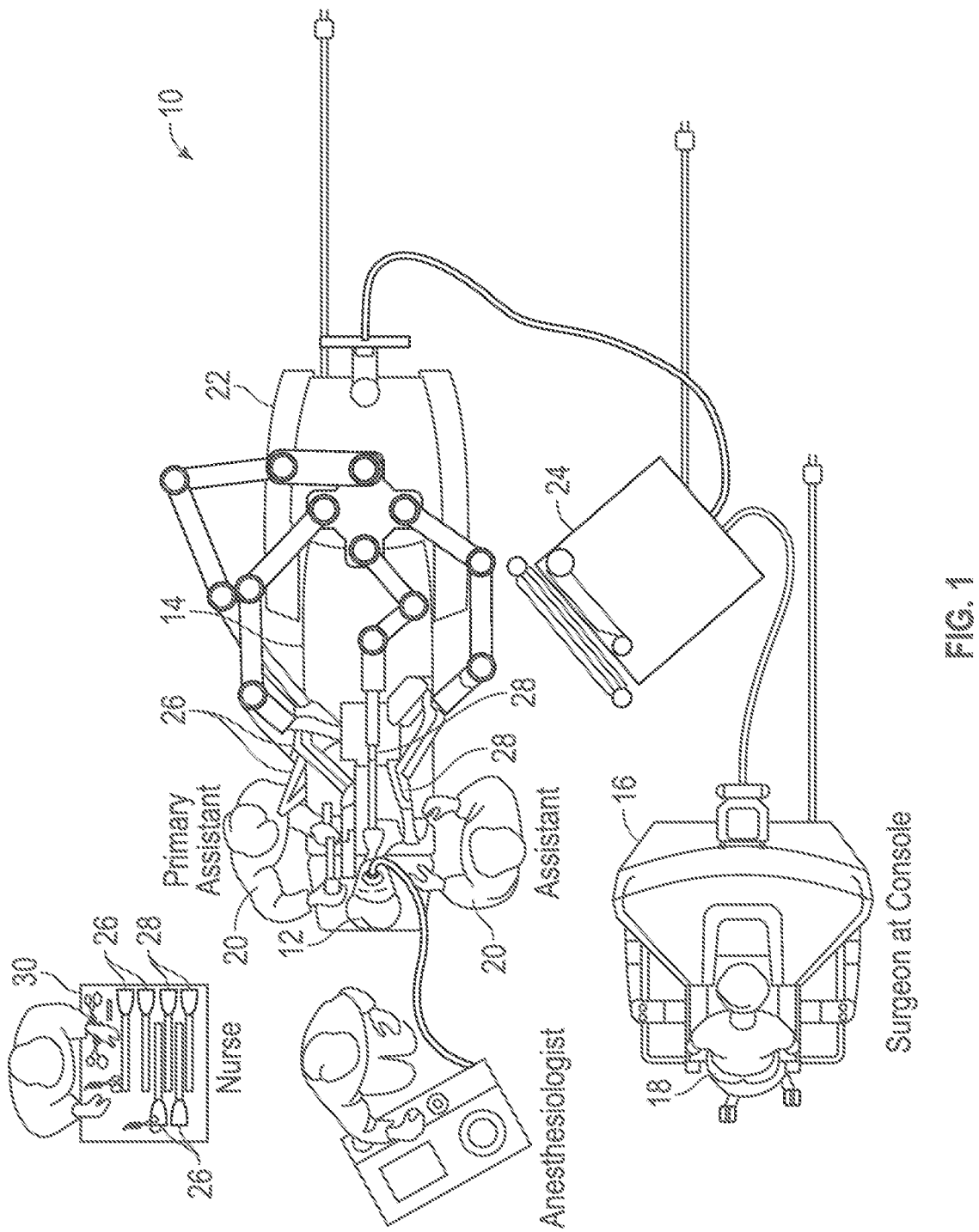
FIG. 1 is a plan view of a minimally invasive teleoperated surgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the scope of this description and the claims. In some instances, well-known circuits, structures, or techniques have not been shown or described in detail in order not to obscure the invention. Like numbers in two or more figures represent the same or similar elements.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci® Surgical System (specifically, a Model IS4000, marketed as the da Vinci® Xi™ HD™ Surgical System), commercialized by Intuitive Surgical, Inc. of Sunnyvale, Calif.

Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000 da Vinci® Xi™ Surgical System, the Model IS3000 da Vinci Si® Surgical System) are merely exemplary and are not to be considered as limiting the scope of the inventive aspects disclosed herein.

In accordance with various aspects, the present disclosure describes a surgical planning tool that includes a medical device configured to video record the performance of surgical procedures. The video recordings can be embedded with various metadata, e.g., highlights made by a medical person. Additionally, the video recordings can be tagged with various metadata. e.g., text annotations describing certain subject matter of the video, the identity of the patient to whom the video recording corresponds, biographical or medical information about the patient, and the like. In one aspect, tagged metadata is embedded in the video recordings.

In accordance with further aspects, the present disclosure describes a teleoperated medical device that includes a surgical instrument used to perform at least one surgical activity during a surgical procedure. A surgical instrument typically has a limited useful lifetime during which it can be reliably used to perform the surgical activity. In some embodiments, a lifetime is indicated as a count of a number of surgeries in which it is permissible to use a surgical instrument. For example, an instrument having a lifetime count of ten is permitted to be used in ten more surgeries, Conversely, for example, an instrument having a lifetime count of five is permitted to be used in five more surgeries.

Different surgical instruments are used to perform different surgical activities. For example, a scalpel is used for dissecting, a needle is used for suturing, and a heat source is used for cauterizing. The use of a surgical instrument to perform its surgical activity during a surgical procedure imparts wear to the surgical instrument. Surgical instrument wear accumulates so as to degrade the utility of the surgical instrument over the course of several surgical procedures to a degree that it is no longer reliably useful for its activity. For example, wear upon a scalpel can involve dulling of the scalpel cutting edges. A surgical instrument that is worn down a degree that it is no longer reliably useful typically is discarded or if feasible, refurbished. In accordance with some embodiments, a record is maintained of remaining useful lifetime of a surgical instrument. Incremental wear imparted to the surgical instrument during a surgical procedure is tracked. The record of remaining useful lifetime of the surgical instrument is updated based upon the incremental wear imparted during the surgical procedure.

In a teleoperated surgical system, different instruments may be used at different stages of a surgical procedure. Moreover, the same instrument may be used in different actuator states at different stages of a surgical procedure. As used herein, the term actuator state refers to a mechanical disposition of a surgical instrument as determined by an actuator, such as a motor, in response to input commands received from a surgeon or other surgical team member.

The video recordings and information structures that associate surgical instrument actuator states with surgical guidance or actuator safety state information can be archived on an electronic medical record database implemented locally or on a cloud data storage service. The video recordings can be made available to interested health care providers. The information structures can be made available for use with the teleoperated medical device to provide surgical guidance and to control surgical instrument actuator state during performance of at least one surgical activity during a surgical procedure.

Health care providers can search the medical device database based upon surgeon skill level for videos and information structure relationships of interest using the metadata tags described above. Additionally, in one aspect, the surgical planning tool includes a computer-based pattern matching and analysis algorithm. In one aspect, the pattern-matching algorithm culls through the videos stored on the electronic medical record database to identify correlations between visual characteristics in the video recordings and associated metadata tags made by medical persons. The surgical planning tool can apply these correlations to newly encountered anatomy, and thereby assist medical persons performing a procedure in making determinations about patient anatomy, preferred surgical approaches, disease states, potential complications, etc.

In another aspect, a pattern matching algorithm culls through videos stored on the electronic medical record database to identify correlations between visual characteristics in the video recordings to identify surgical activities that contribute to instrument degradation. Some routine surgical activities result in predictable rates of instrument degradation so that an instrument can be designated for efficacy and safety reasons as suitable for a fixed number of surgical uses, referred to as "lifetimes". For example, an instrument that has 'x' number of lifetimes for its intended use is eligible for its intended use in 'x' surgeries before it must be refurbished or discarded. Certain irregular surgical uses of an instrument can accelerate its degradation. Surgical uses of individual instruments are tracked. A surgical planning tool can apply correlations between surgical activities and instrument wear-rate for to individual surgical instruments for inventory planning purposes to determine when to replace or refurbish individual surgical instruments based upon their individual remaining lifetimes.

Minimally Invasive Teleoperated Surgical System Referring now to the drawings, in which like reference numerals represent like parts throughout the several views, FIG. 1 is a plan view of a minimally invasive teleoperated surgical system 10, typically used for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes a patient-side cart 22 and an electronics cart 24. The patient-side cart 22 can manipulate at least one removably coupled surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which can be manipulated by the patient-side cart 22 to orient the endoscope 28. Computer processors located on the electronics cart 24 can be used to process the images of the surgical site for subsequent display to the surgeon 18 through the surgeon's console 16. The number of surgical instruments 26 used at one time will generally depend on the diagnostic or surgical procedure and the space constraints within the operating room among other factors. If it is necessary to change one or more of the surgical instruments 26 being used during a procedure, an assistant 20 can remove the surgical instrument 26 from the patient-side cart 22, and replace it with another surgical instrument 26 from a tray 30 in the operating room.

Figure 2:
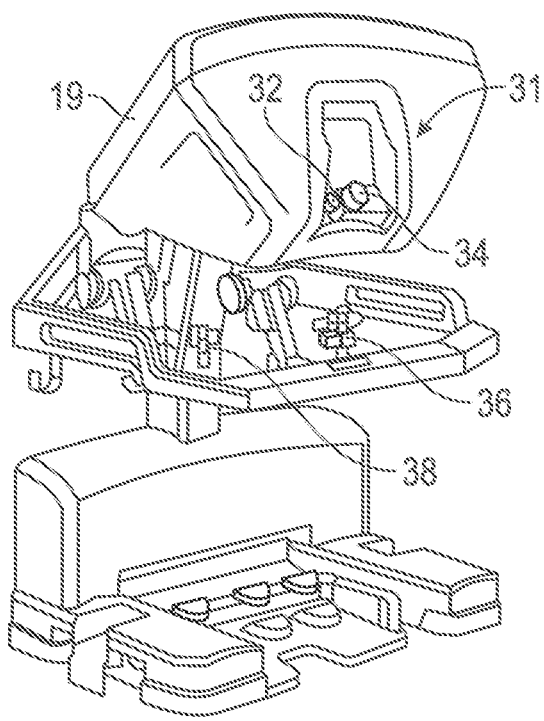
FIG. 2 is a perspective view of a surgeon's console.

FIG. 2 is a perspective view of the surgeon's console 16. The surgeon's console 16 includes a left eye display 32 and a right eye display 34 for presenting the surgeon 18 with a coordinated stereoscopic view of the surgical site that enables depth perception. The console 16 further includes one or more control inputs 36. One or more surgical instruments installed for use on the patient-side cart 22 (shown in FIG. 1) move in response to surgeon 18's manipulation of the one or more control inputs 36. The control inputs 36 can provide the same mechanical degrees of freedom as their associated surgical instruments 26 (shown in FIG. 1) to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36.

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote surgical procedures.

Figure 3:
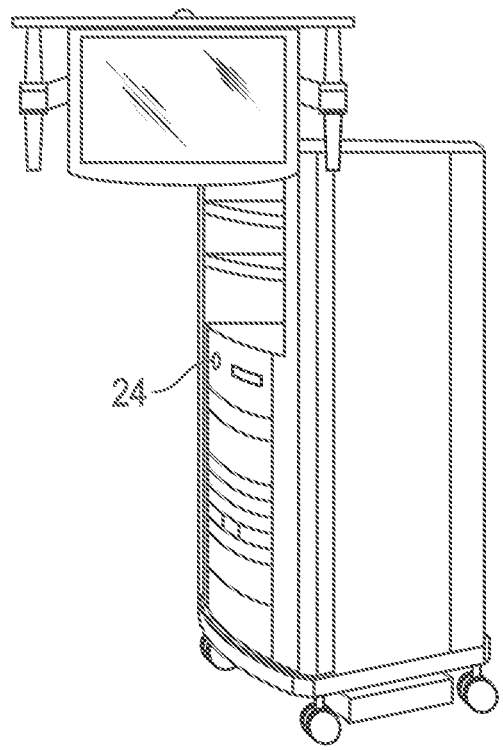
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console, or on another suitable display located locally and/or remotely. For example, if a stereoscopic endoscope is used, a computer processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
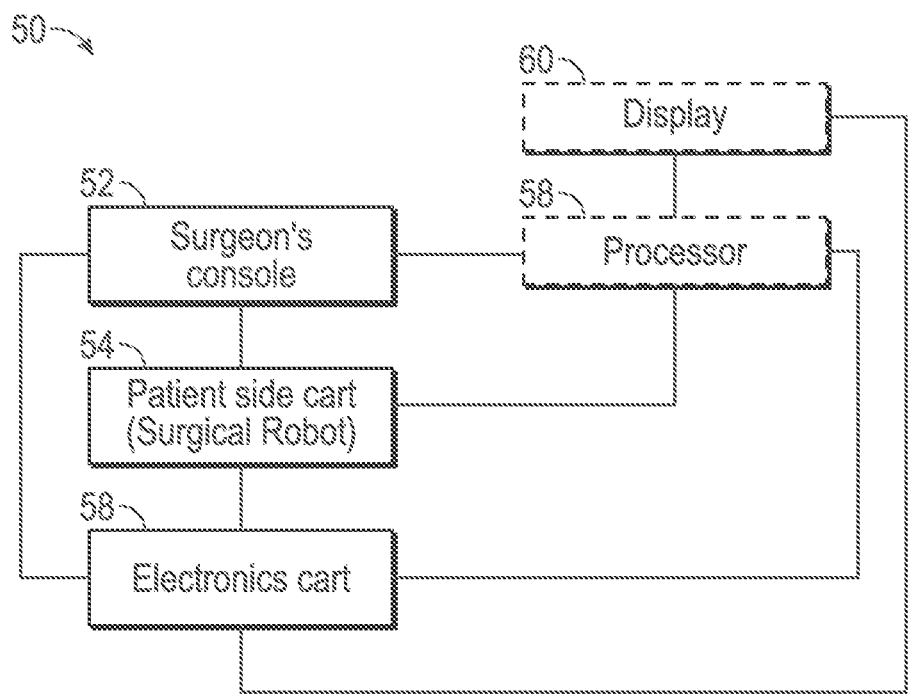
FIG. 4 is a diagrammatic illustration of a teleoperated surgical system.

FIG. 4 diagrammatically illustrates a teleoperated surgical system 50 (such as the minimally invasive teleoperated surgical system 10 of FIG. 1). A surgeon's console 52 (such as surgeon's console 16 in FIG. 1) can be used by a surgeon to control a patient-side cart 54 (such as patent-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data processing boards purposed for executing computer readable code stored in a non-volatile memory device of the computer processor. In one aspect, the computer processor can process the captured images in a variety of ways prior to any subsequent display. For example, the computer processor can overlay the captured images with a virtual control interface prior to displaying the combined images to the surgeon via the surgeon's console 52.

Additionally or in the alternative, the captured images can undergo image processing by a computer processor located outside of electronics cart 56. In one aspect, teleoperated surgical system 50 includes an optional computer processor 58 (as indicated by dashed line) similar to the computer processor located on electronics cart 56, and patient-side cart 54 outputs the captured images to computer processor 58 for image processing prior to display on the surgeon's console 52. In another aspect, captured images first undergo image processing by the computer processor on electronics cart 56 and then undergo additional image processing by computer processor 58 prior to display on the surgeon's console 52. Teleoperated surgical system 50 can include an optional display 60, as indicated by dashed line. Display 60 is coupled with the computer processor located on the electronics cart 56 and with computer processor 58, and captured images processed by these computer processors can be displayed on display 60 in addition to being displayed on a display of the surgeon's console 52.

Figure 5:
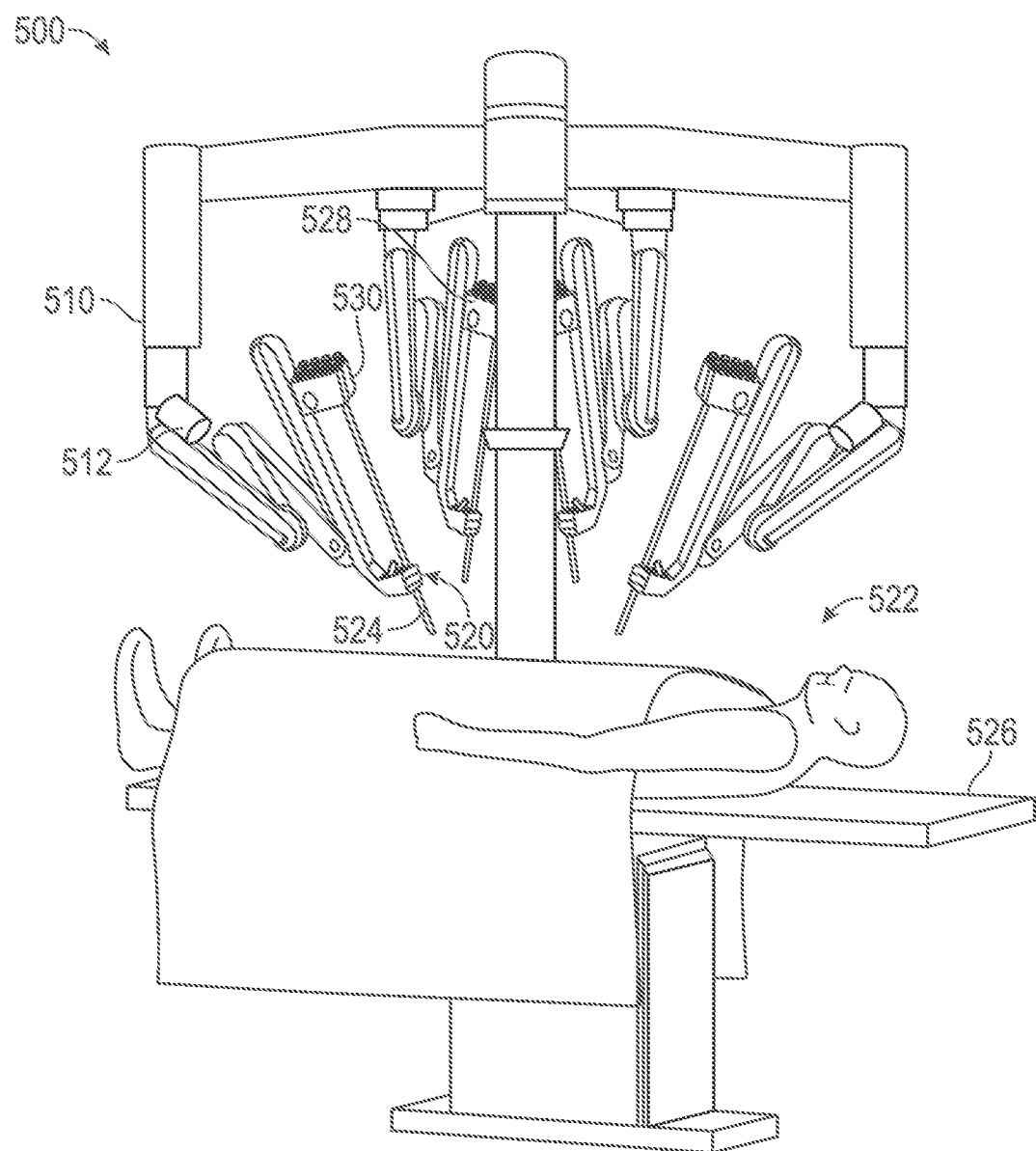
FIG. 5 is a perspective view of a patient-side cart.

FIG. 5 is a perspective view of a patient-side cart 500 of a minimally invasive teleoperated surgical system, in accordance with embodiments of the present invention. The patient-side cart 500 includes one or more support assemblies 510. A surgical instrument manipulator 512 is mounted at the end of each support assembly 510. Additionally, each support assembly 510 can optionally include one or more unpowered, lockable setup joints that are used to position the attached surgical instrument manipulator 512 with reference to the patient for surgery. As depicted, the patient-side cart 500 rests on the floor. In other embodiments, operative portions of the patient-side cart can be mounted to a wall, to the ceiling, to the operating table 526 that also supports the patient's body 522, or to other operating room equipment. Further, while the patient-side cart 500 is shown as including four surgical instrument manipulators 512, more or fewer surgical instrument manipulators 512 may be used.

A functional minimally invasive teleoperated surgical system will generally include a vision system portion that enables a user of the teleoperated surgical system to view the surgical site from outside the patient's body 522. The vision system typically includes a camera instrument 528 for capturing video images and one or more video displays for displaying the captured video images. In some surgical system configurations, the camera instrument 528 includes optics that transfer the images from a distal end of the camera instrument 528 to one or more imaging sensors (e.g., CCD or CMOS sensors) outside of the patient's body 522. Alternatively, the imaging sensor(s) can be positioned at the distal end of the camera instrument 528, and the signals produced by the sensor(s) can be transmitted along a lead or wirelessly for processing and display on the one or more video displays. One example of a video display is the stereoscopic display on the surgeon's console in surgical systems commercialized by Intuitive Surgical, Inc., Sunnyvale, Calif.

Referring to FIG. 5, mounted to each surgical instrument manipulator 512 is a surgical instrument 520 that operates at a surgical site within the patient's body 522. Each surgical instrument manipulator 512 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 512 to move its associated surgical instrument around a center of motion on the instrument that stays stationary with reference to the patient, and this center of motion is typically located at the position where the instrument enters the body.

In one aspect, surgical instruments 520 are controlled through computer-assisted teleoperation. A functional minimally invasive teleoperated surgical system includes a control input that receives inputs from a user of the teleoperated surgical system (e.g., a surgeon or other medical person). The control input is in communication with one or more computer-controlled teleoperated actuators, such as one or more motors to which surgical instrument 520 is coupled. In this manner, the surgical instrument 520 moves in response to a medical person's movements of the control input. In one aspect, one or more control inputs are included in a surgeon's console such as surgeon's console 16 shown at FIG. 2. A surgeon can manipulate control inputs 36 of surgeon's console 16 to operate teleoperated actuators of patient-side cart 500. The forces generated by the teleoperated actuators are transferred via drivetrain mechanisms, which transmit the forces from the teleoperated actuators to the surgical instrument 520.

Referring to FIG. 5, in one aspect, a surgical instrument 520 and a cannula 524 are removably coupled to manipulator 512, with the surgical instrument 520 inserted through the cannula 524. One or more teleoperated actuators of the manipulator 512 move the surgical instrument 512 as a whole. The manipulator 512 further includes an instrument carriage 530. The surgical instrument 520 is detachably connected to the instrument carriage 530. In one aspect, the instrument carriage 530 houses one or more teleoperated actuators inside that provide a number of controller motions that the surgical instrument 520 translates into a variety of movements of an end effector on the surgical instrument 520. Thus the teleoperated actuators in the instrument carriage 530 move only one or more components of the surgical instrument 520 rather than the instrument as a whole. Inputs to control either the instrument as a whole or the instrument's components are such that the input provided by a surgeon or other medical person to the control input (a "master" command) is translated into a corresponding action by the surgical instrument (a "slave" response). In an alternate embodiment, instrument carriage 530 does not house teleoperated actuators. Teleoperated actuators that enable the variety of movements of the end effector of the surgical instrument 520 are housed in a location remote from the instrument carriage 530, e.g., elsewhere on patient-side cart 500. A cable-based force transmission mechanism or the like is used to transfer the motions of each of the remotely located teleoperated actuators to a corresponding instrument-interfacing actuator output located on instrument carriage 530. In some embodiments, the surgical instrument 520 is mechanically coupled to a first actuator, which controls a first motion of the surgical instrument such as longitudinal (z-axis) rotation. The surgical instrument 520 is mechanically coupled to a second actuator, which controls second motion of the surgical instrument such as two-dimensional (x, y) motion. The surgical instrument 520 is mechanically coupled to a third actuator, which controls third motion of the surgical instrument such as opening and closing or a jaws end effector.

FIG. 6A is a side view of a surgical instrument 520, which includes a distal portion 650 and a proximal control mechanism 640 coupled by an elongate tube 610 having an elongate tube centerline axis 611. The surgical instrument 520 is configured to be inserted into a patient's body and is used to carry out surgical or diagnostic procedures. The distal portion 650 of the surgical instrument 520 can provide any of a variety of end effectors 654, such as the forceps shown, a needle driver, a cautery device, a cutting tool, an imaging device (e.g., an endoscope or ultrasound probe), or the like. The surgical end effector 654 can include a functional mechanical degree of freedom, such as jaws that open or close, or a knife that translates along a path. In the embodiment shown, the end effector 654 is coupled to the elongate tube 610 by a wrist 652 that allows the end effector to be oriented relative to the elongate tube centerline axis 611. Surgical instrument 520 can also contain stored (e.g., on a semiconductor memory device 660 associated with the instrument) information, which may be permanent or may be updatable by a surgical system configured to operate the surgical instrument 520. In some embodiments, a semiconductor memory device 660 associated with an instrument tracking device 662 is associated with the instrument 520. In some embodiments, the instrument tracking device 662 includes a radio frequency identification device (RFID) device. Accordingly, the surgical system may provide for either one-way or two-way information communication between the surgical instrument 520 and one or more components of the surgical system.

FIG. 6B is an illustrative drawing representing an RFID tracking device 662 associated with an instrument 520 in accordance with some embodiments. The RFID device 662 includes a storage device 660 that includes an information structure 664 that associates device identifier information 666 with remaining device lifetime information 668. The RFID device 662 includes a transceiver circuitry 670 to send and receive information wirelessly. The RFID device 662 includes control logic circuitry 672 to control the storage device 660 and the transceiver 670.

Figure 7:
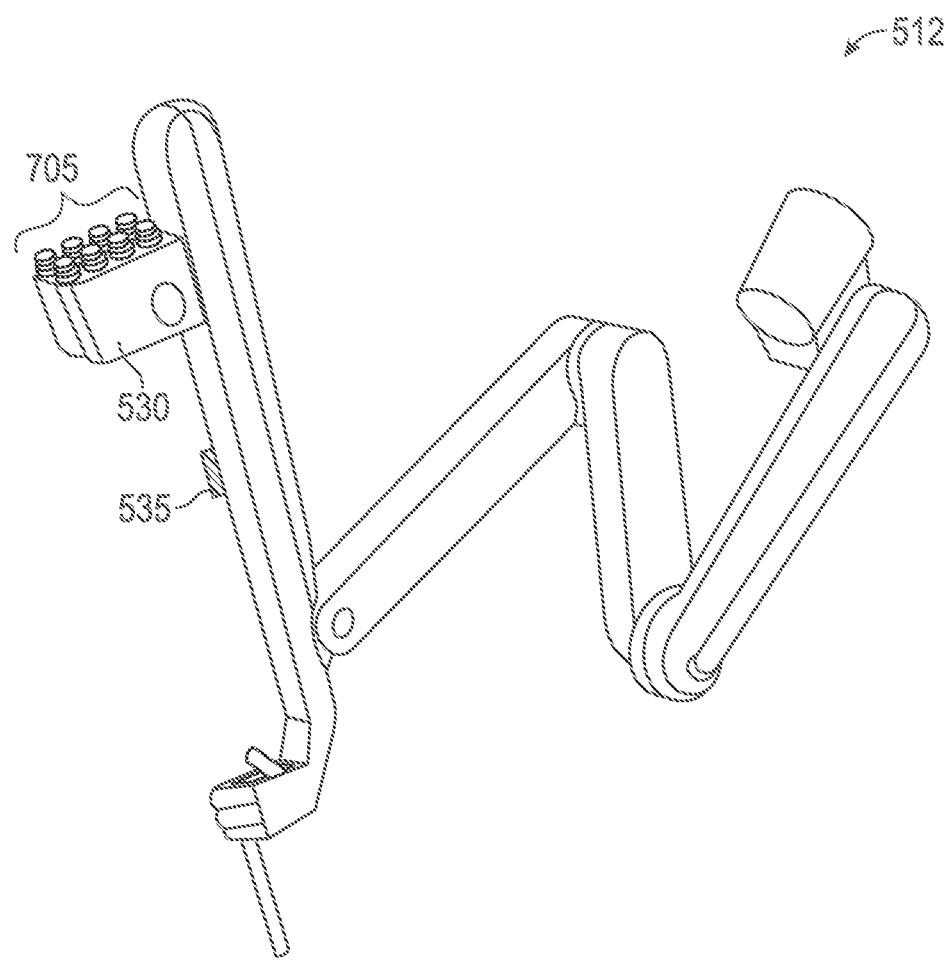
FIG. 7 is a perspective view of an instrument manipulator.

FIG. 7 is a perspective view of surgical instrument manipulator 512. Instrument manipulator 512 is shown with no surgical instrument installed. Instrument manipulator 512 includes an instrument carriage 530 to which a surgical instrument (e.g., surgical instrument 520) can be detachably connected. Instrument carriage 530 houses a plurality of teleoperated actuators. In some embodiments, an RFID reader 535 is disposed upon the instrument manipulator 512 in a location to read the contents of the storage device 660 within an RFID device 662 associated with an instrument attached to the manipulator 512. Each teleoperated actuator includes an actuator output 705. When a surgical instrument is installed onto instrument manipulator 512, one or more instrument inputs (not shown) of an instrument proximal control mechanism (e.g., proximal control mechanism 640 at FIG. 6) are mechanically coupled with corresponding actuator outputs 705. In one aspect, this mechanical coupling is direct, with actuator outputs 705 directly contacting corresponding instrument inputs. In another aspect, this mechanical coupling occurs through an intermediate interface, such as a component of a drape configured to provide a sterile barrier between the instrument manipulator 512 an associated surgical instrument.

In one aspect, movement of one or more instrument inputs by corresponding teleoperated actuators results in a movement of a surgical instrument mechanical degree of freedom. For example, in one aspect, the surgical instrument installed on instrument manipulator 512 is surgical instrument 520, shown at FIG. 6. Referring to FIG. 6, in one aspect, movement of one or more instrument inputs of proximal control mechanism 640 by corresponding teleoperated actuators rotates elongate tube 610 (and the attached wrist 652 and end effector 654) relative to the proximal control mechanism 640 about elongate tube centerline axis 611. In another aspect, movement of one or more instrument inputs by corresponding teleoperated actuators results in a movement of wrist 652, orienting the end effector 654 relative to the elongate tube centerline axis 611. In another aspect, movement of one or more instrument inputs by corresponding teleoperated actuators results in a movement of one or more moveable elements of the end effector 654 (e.g., a jaw member, a knife member, etc.). Accordingly, various mechanical degrees of freedom of a surgical instrument installed onto an instrument manipulator 512 can be moved by operation of the teleoperated actuators of instrument carriage 530.

Annotating a Recorded Video

Figure 8:
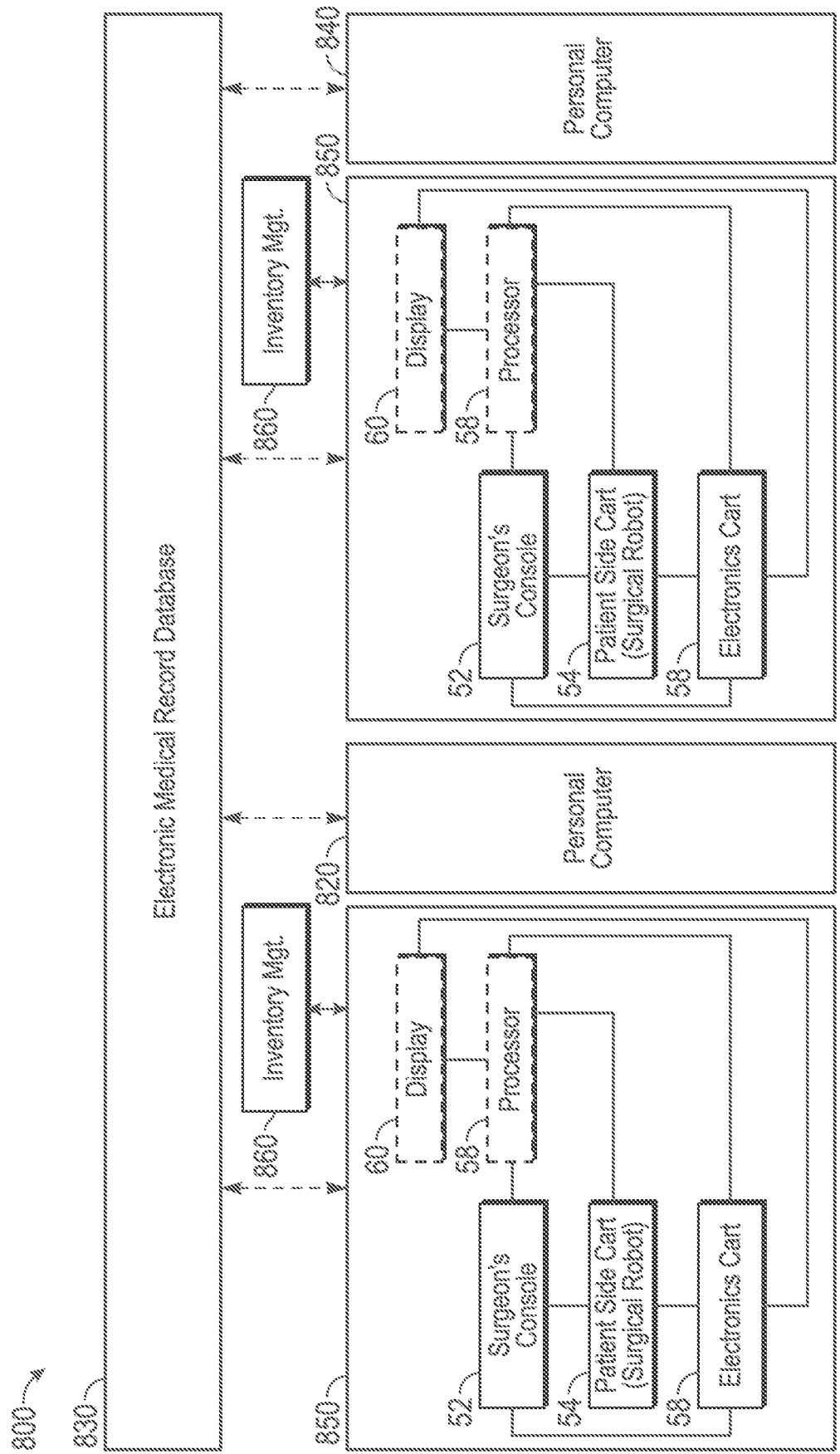
FIG. 8 is a diagrammatic illustration of a surgical planning tool.

FIG. 8 shows a schematic diagram of an exemplary surgical planning tool 800. In one aspect, surgical planning tool 800 includes a teleoperated surgical system 850 in data communication with an electronic medical device record database 830 and an instrument inventory management system 860. Teleoperated surgical system 850 shown here is similar to teleoperated surgical system 850 shown at FIG. 4. In one aspect, electronic medical record database 830 includes the medical records of patients that have undergone treatment at a particular hospital. Database 830 and instrument inventory management system 860 can be implemented on a server located on-site at the hospital. The medical record entries contained in the database 830 and management system 860 can be accessed from hospital computers through an intranet network. Alternatively, database 830 and management system 860 can be implemented on a remote server located off-site from the hospital, e.g., using one of a number of cloud data storage services. In this case, medical record entries of database 830 and management system 860 are stored on the cloud server, and can be accessed by a computer with internet access.

In one aspect, a surgical procedure is performed on a first patient using teleoperated surgical system 850. An imaging device associated with teleoperated surgical system 850 captures images of the surgical site and displays the captured images as frames of a video on a display of surgeon's console 52. In one aspect, a medical person at surgeon's console 52 highlights or annotates certain patient anatomy shown in the displayed video using an input device of surgeon's console 52. An example of such an input device is control input 36 shown at FIG. 2, which is coupled to a cursor that operates in conjunction with a graphic user interface overlaid onto the displayed video. The graphic user interface can include a QWERTY keyboard, a pointing device such as a mouse and an interactive screen display, a touch-screen display, or other means for data or text entry. Accordingly, the medical person can highlight certain tissue of interest in the displayed image or enter a text annotation.

In one aspect, the surgical site video is additionally displayed on a display located on electronics cart 56. In one aspect, the display of electronics cart is a touch-screen user interface usable by a medical person to highlight and annotate certain portions of patient anatomy shown on an image that is displayed for viewing on the display on the electronics cart. A user, by touching portions of patient anatomy displayed on the touch-screen user interface, can highlight portions of the displayed image. Additionally, a graphic interface including a QWERTY keyboard can be overlaid on the displayed image. A user can use the QWERTY keyboard to enter text annotations.

In one aspect, the surgical site video captured by the imaging device associated with teleoperated surgical system 850 is recorded by the teleoperated surgical system 850, and stored on database 830, in addition to being displayed in real time or near real time to a user. Highlights and/or annotations associated with the recorded video that were made by the user can also be stored on database 830. In one aspect, the highlights made by the user are embedded with the recorded video prior to its storage on database 830. At a later time, the recorded video can be retrieved for viewing. In one aspect, a viewer of the recorded video can select whether the highlights are displayed or suppressed from view. Similarly, annotations associated with the recorded video can also be stored on database 830. In one aspect, the annotations made by the user are used to tag the recorded video, and can be used to provide as a means of identifying the subject matter contained in the recorded video. For example, one annotation may describe conditions of a certain disease state. This annotation is used to tag the recorded video. At a later time, a person desiring to view recorded procedures concerning this disease state can locate the video using a key word search.

Retrieval of Stored Video

In some cases, it is desirable for a medical person to be able to view video recordings of past surgical procedures performed on a given patient. In one aspect, a patient who previously underwent a first surgical procedure to treat a medical condition subsequently requires a second surgical procedure to treat recurrence of the same medical condition or to treat anatomy located nearby to the surgical site of the first surgical procedure. In one aspect, the surgical site events of the first surgical procedure were captured in a surgical site video recording, and the video recording was archived in database 830 as part of the patient's electronic medical records. Prior to performing the second surgical procedure on the patient, a medical person can perform a search of database 830 to locate the video recording of the patient's earlier surgical procedure.

In some cases, it is desirable for a medical person planning to perform a surgical procedure on a patient to be able to view video recordings of similar surgical procedures performed on persons having certain characteristics similar to the patient. In one aspect, surgical site video recordings of surgical procedures can be tagged with metadata information such as the patient's age, gender, body mass index, genetic information, type of procedure the patient underwent, etc., before each video recording is archived in database 830. In one aspect, the metadata information used to tag a video recording is automatically retrieved from a patient's then-existing medical records, and then used to tag the video recording before the video recording is archived in database 830. Accordingly, prior to performing a medical procedure on a patient, a medical person can search database 830 for video recordings of similar procedures performed on patients sharing certain characteristics in common with the patient. For example, if the medical person is planning to use teleoperated surgical system 850 to perform a prostatectomy on a 65 year-old male patient with an elevated body mass index using, the medical person can search database 830 for surgical site video recordings of prostatectomies performed using teleoperated surgical system 850 on other males of similar age and having similarly elevated body mass index.

In one aspect, a video recording of a surgical procedure is communicated by database 830 to an optional personal computer 820 (as indicated by dashed line), and made available for viewing by a medical person who plans to perform a surgical procedure. Additionally or in the alternative, the video recording of the earlier surgical procedure can be communicated by database 830 to teleoperated surgical system 850, and made available for viewing pre-operatively or intraoperatively. In one aspect, the video recording is displayed by teleoperated surgical system 850 on a display located on surgeon's console 52. In another aspect, the video recording of the first surgical procedure is displayed on a display located on electronics cart 56.

Cloud-Based Video Database

In one aspect, database 830 is implemented on a remote server using a cloud data storage service and is accessible by multiple health care providers. Referring to FIG. 8, as shown by dashed line, surgical planning tool 800 optionally includes teleoperated surgical system 850 (as indicated by dashed line) and personal computer 840 (as indicated by dashed line). In one aspect, teleoperated surgical system 850 is similar to teleoperated surgical system 850 and personal computer 840 is similar to personal computer 820, except that teleoperated surgical system 850 and personal computer 820 are located at a first health care provider and teleoperated surgical system 850 and personal computer 840 are located at a second health care provider. In one aspect, a first patient requires surgical treatment of a medical condition, and undergoes a surgical procedure using teleoperated surgical system 850 at the first health care provider. A video recording of the surgical procedure is archived on database 830. At a later time, a second patient requires surgical treatment of the same medical condition, and plans to receive surgical treatment using teleoperated surgical system 850 at the second health care provider. Prior to performing the surgical procedure on the second patient, a medical person accesses database 830 through a secure internet connection and searches database 830 for surgical site video recordings of similar procedures. In one aspect, the medical person treating the second patient is able to retrieve from database 830 the video recording of first patient's surgical procedure, without acquiring knowledge of the identity of the first patient. In this manner, the privacy of the first patient is maintained. In one aspect, the video recording of the first patient's surgical procedure includes highlights and/or annotations made by the medical person who treated the first patient.

Computer Based Pattern Matching and Analysis

Surgical planning tool 800 can includes a pattern matching and analysis algorithm implemented in the form of computer executable code. In one aspect, the pattern matching and analysis algorithm is stored in a non-volatile memory device of surgical planning tool 800, and is configured to analyze the video recordings archived in database 830. As discussed previously, each of the video recordings archived in database 830 can be tagged and/or embedded with certain metadata information. This metadata information can include patient information such as patient age, gender, and other information describing the patient's health or medical history. Additionally, as discussed previously, the metadata information can include highlights or annotations made by a medical person. In one aspect, these highlights and annotations are embedded with the video recording and archived together with the video in database 830.

In one aspect, pattern matching and analysis algorithm includes an image analysis component that identifies patterns in shapes and colors that are shared amongst multiple video recordings stored on database 830. The pattern matching and analysis algorithm then reviews the tagged metadata associated with this subset of video recordings to determine whether any words or phrases are frequently associated with videos within this subset. These analyses performed by pattern matching and analysis algorithm can be used to assist medical persons in making determinations about patient anatomy, preferred surgical approaches, disease states, potential complications, etc.

A Method of Using a Surgical Planning Tool

Figure 9:
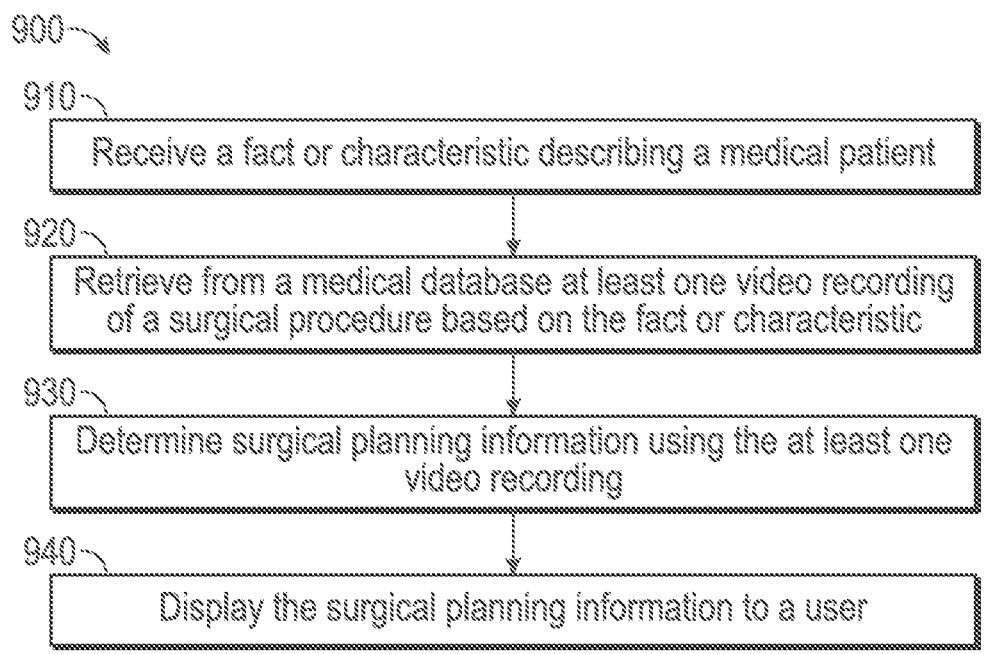
FIG. 9 is a flow diagram of a method of using a surgical planning tool.

FIG. 9 shows a method 900 of using a surgical planning tool. In one aspect, the surgical planning tool is similar to surgical planning tool 800 at FIG. 8. At 910, a fact or characteristic describing a medical patient, e.g., a medical condition suffered by a patient, is received by a medical device. Medical device can receive this fact or circumstance via a user interface located on a teleoperated surgical system (e.g., teleoperated surgical system 10 at FIG. 1 or teleoperated surgical system 50 at FIG. 4), or alternatively, through a personal computer similar to personal computer 820 at FIG. 2. At 920, the medical device uses the fact or characteristic received at 910 to retrieve at least one relevant video recording of a surgical procedure from a medical device database. At 930, the medical device uses the video recordings to determine surgical planning information. In one aspect, the surgical planning information includes the types of instruments used in the recorded procedure. At 940, the medical device displays to a user the surgical planning information determined at 930.

A Method of Surgical Instrument Inventory Management Based upon Observation of Surgical Instrument Usage Chart 1 identifies several example surgical instruments and the corresponding incremental lifetime degradation resulting from routine in-surgery use, irregular in-surgical use, and sterilization in accordance with some embodiments.

CHART 1

| Instrument Name | Total Lifetimes for new instrument | Total Lifetimes for refurbished instrument | Lifetime decrement - per routine in-surgery usage | Lifetime decrement - Per irregular in-surgery usage | Lifetime decrement - Per sterilization |
|---|---|---|---|---|---|
| Suturing instr | | | | | |
| Scalpel instr | | | | | |
| Cauterizing instr | | | | | |
| Scissors instr | | | | | |
| Other? | | | | | |

In some embodiments, an instrument can be refurbished to add lifetimes i.e. additional surgical uses. However a refurbished instrument may start with fewer lifetimes than a new instrument. In some embodiments, the number of surgeries in which a surgical instrument can be used varies with the use of the instrument. Irregular use can result in more rapid degradation of the instrument. For example, an irregular use of a scissors instrument to perform suturing can result in accelerated degradation. Moreover, a sterilization of an instrument can involve high temperatures and chemical treatment, which can result in instrument wear.

Figure 10:
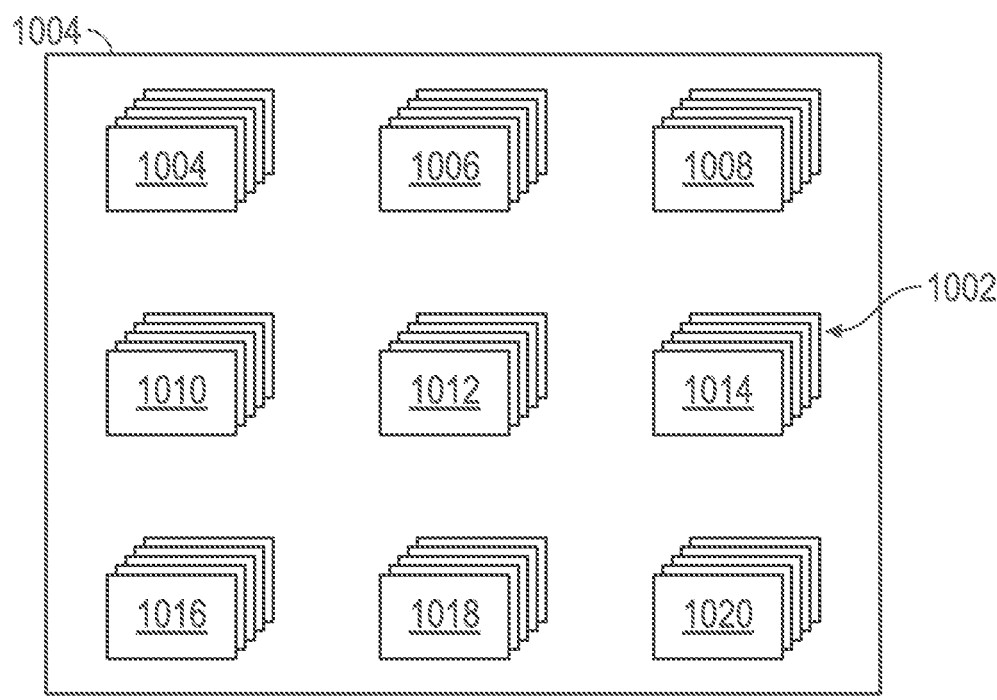
FIG. 10 is an illustrative drawing representing storage atlas in a computer readable storage device in accordance with some embodiments.

FIG. 10 is an illustrative drawing representing storage atlas in a computer readable storage device 1004 in accordance with some embodiments. The storage atlas 1002 includes first information structures 1006 that indicate instances of previously performed surgical procedures. Second information structures 1008 associate surgical procedures with surgical activities performed and surgical instruments used during the surgical procedure. Third information structures 1010 associate surgical activities with surgical instrument actuation states. Fourth information structures 1012 associate routine surgical instrument use, lifetime decrements with surgical instrument actuation states. Fifth information structures 1014 associate non-routine surgical instrument use, lifetime decrements with surgical instrument actuation states. Sixth information structures 1016 associate surgical instrument sterilization, lifetime decrements with sterilization events. Seventh information structures 1018 that associate video images of surgical scenes recorded during surgical procedures with instrument actuation states recorded during the surgical procedures. In some embodiments, the various information structures 1004-1018 are evaluated to produce eighth information structures 1020 that associate surgical activities with surgical instrument activity states and with surgical instrument lifetime decrements.

Figures 11, 12A, 12B, 12C:
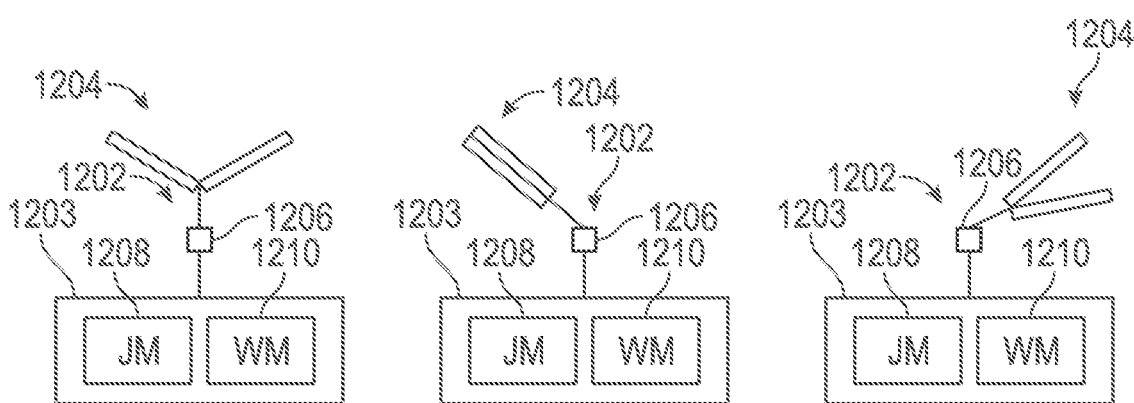
FIG. 11 is an illustrative drawing representing an example instance of the seventh information structure included within the atlas in the storage device, which associates recorded video images from an individual surgery with corresponding surgical instrument actuator state information in accordance with some embodiments.
FIGS. 12A-12C are illustrative drawings showing an example surgical instrument and an actuator assembly in which the surgical instrument is shown in three different example operational states in accordance with some embodiments.

FIG. 11 is an illustrative drawing representing an example instance of the seventh information structure 1018 included within the atlas 1002 in the storage device 1004, which associates recorded video images from an individual surgery with corresponding surgical instrument actuator state information in accordance with some embodiments. In one aspect, video images of patient anatomy structures and instruments used to operate upon those anatomical structures during a surgery and corresponding surgical instrument actuator states are recorded and time stamped (t1, t2 ... tn) during a surgery to produce a chronological record of surgical activities and corresponding surgical instrument actuator states during the surgical procedure. The time stamps are used to temporally align video images with surgical instrument actuator states.

During a surgery, a user may annotate the video recording and the surgical instrument actuation state recording with metadata that indicate corresponding surgical activity. The annotation may include one or more of or a combination of written notes tagged to video information and/or surgical instrument actuation state information, coloring or highlighting (e.g., telestration) of images in the video recordings, for example. The annotations may be time stamped for use to temporally align them with corresponding video recording information and corresponding recorded surgical instrument state information.

During a teleoperated surgical procedure, a surgical activity can which involves use of at least one surgical instrument. During the surgical activity, the surgical instrument is operated, under surgeon control, in one or more actuator states. Operation of the surgical instrument in support of the surgical activity in the one or more surgical states can result in degradation of the instrument's efficacy for its intended use. As explained more fully below, to keep track of this reduction in efficacy, a record indicating the instrument's remaining lifetime is modified, e. g., a lifetime count may be decremented in response to the instrument's usage in the surgical activity.

FIGS. 12A-12C are illustrative drawings showing an example surgical instrument 1202 and an actuator assembly 1203 in which the surgical instrument is shown in three different example operational states in accordance with some embodiments. The example instrument 1202 includes a jaw end effector 1204 that can transition between open and closed states and a continuum of partially opened/partially closed states in between. The example instrument 1202 also includes a two degree of freedom (2-dof) wrist 1206 that can move between different two-dimensional (x, y) positional states. The example actuator assembly 1203 includes a first actuator 1208, which in some embodiments includes a jaw motor (JM) used to actuate the jaw end effector 1204. The example actuator assembly 1203 includes a second actuator 1210, which in some embodiments includes a wrist motor (WM) used to actuate the wrist 1206. During a surgery, the surgical instrument 1202 may transition through multiple actuation states corresponding to different activities during a surgical procedure. As represented in FIG. 12A, for example, a surgical procedure may involve a first surgical activity in which the first actuator 1208 (the JM) disposes the jaw end effector 1204 to a fully open state and the second actuator 1210 the (WM) disposes the wrist 1206 to a first positional state (x1, y1). As represented in FIG. 12B, for example, the surgical procedure may involve a second surgical activity in which the first actuator 1208 transitions the jaw end effector 1204 to a fully closed state and the second actuator 1210 transitions the wrist 1206 to a second positional state (x2, y2). As represented in FIG. 12C, for example, the surgical procedure may involve a third surgical activity in which the first actuator 1208 disposes the jaw end effector 1104 in a partially open/partially closed state and the second actuator 1210 transitions the wrist 1206 to a third positional state (x3, y3).

Figure 13:
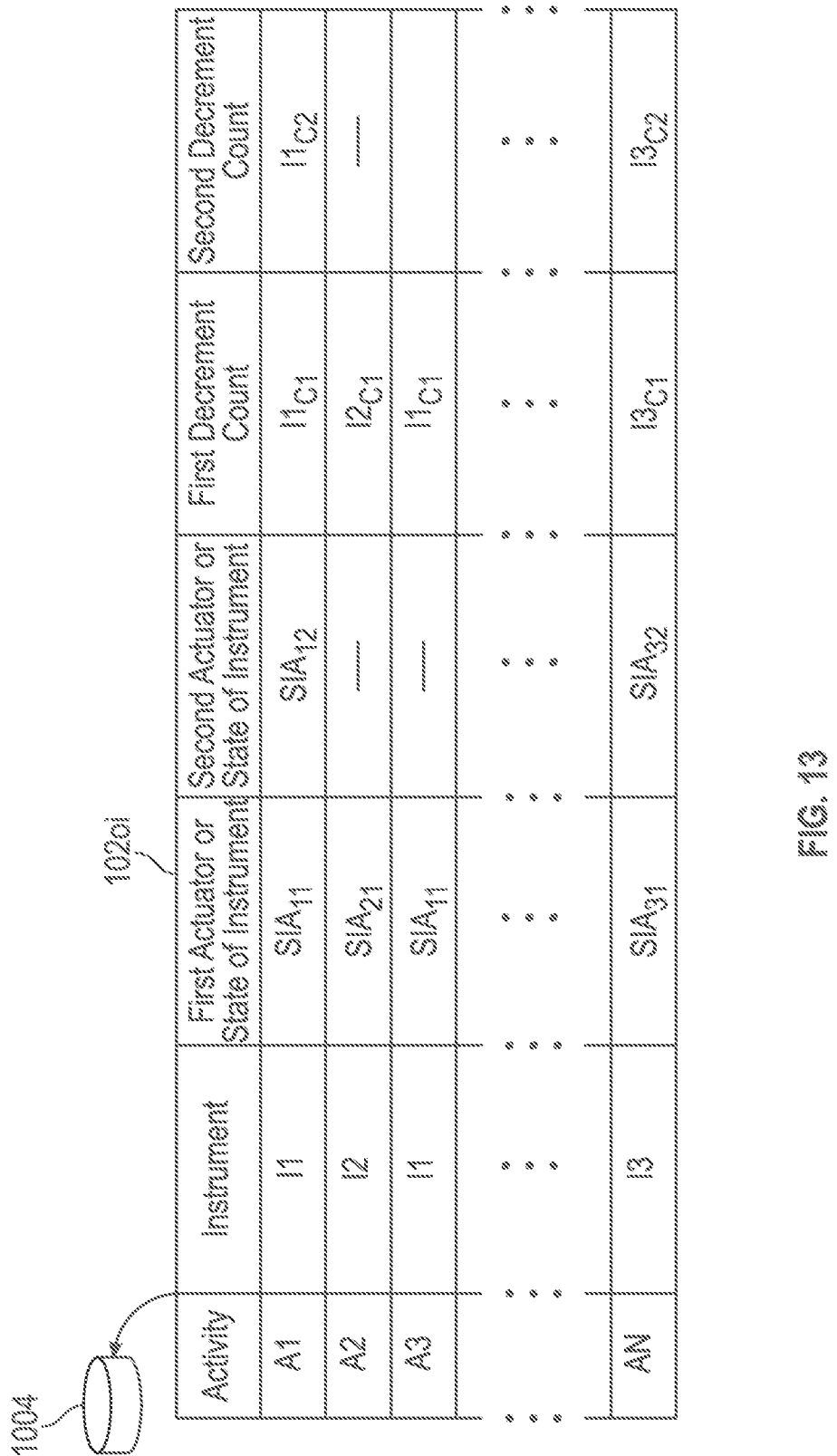
FIG. 13 is an illustrative drawing representing an example instance of the eighth information structure of the atlas stored in the computer readable storage device in accordance with some embodiments.

FIG. 13 is an illustrative drawing representing an example instance 1020$i$ of the eighth information structure 1020 of the atlas 1002 stored in the computer readable storage device 1004 in accordance with some embodiments. The example eighth information structure instance 1020$i$ associates surgical activities during a selected surgical procedure with surgical instrument actuator states that are possible during the activity. The example eighth information structure instance 1020$i$ associates the possible surgical instrument actuator states with corresponding surgical instrument lifetime decrements.

A first column of the example eighth information structure instance 1020$i$ indicates a list of surgical activities, A1, A2. A3 . . . AN to be performed during the example surgical procedure. A second column of the information structure instance 1020$i$ indicates instruments I1, I2, I3 to be used during surgical activities. A third column indicates first possible surgical instrument actuation states that can occur during corresponding surgical activities. A fourth column indicates second possible surgical instrument actuation states that can occur during corresponding surgical activities. Referring to the third and fourth columns, the first instrument I1 can operate in either of two possible surgical instrument actuator (SIA) states, $SIA_{11}$ and $SIA_{12}$. The second instrument I2 can operate in only one surgical instrument actuator state, $SIA_{21}$. The third instrument I3 can operate in either of two possible surgical instrument actuator states, $SIA_{31}$ and $SIA_{32}$. A fifth column indicates lifetime decrements corresponding to corresponding first possible surgical instrument actuation states. A sixth column indicates lifetime decrements corresponding to corresponding second possible surgical instrument actuation states. Referring to the fifth and sixth columns, the first instrument I1 operating in the first instrument's first actuator state $SIA_{11}$ is associated with the first instrument's first decrement count $I1_{C1}$, and the first instrument I1 operating in the first instrument's second actuator state $SIA_{12}$ is associated with the first instrument's second decrement count $I1_{C2}$. The second instrument I2 operating in the second instrument's first actuator state $SIA_{22}$ is associated with the second instrument's first decrement count $I2_{C1}$, and the second instrument I2 operating in the second instrument's second actuator state $SIA_{22}$ is associated with the second instrument's second decrement count $I2_{C2}$. The third instrument I3 operating in the third instrument's first actuator state $SIA_{31}$ is associated with the third instrument's first decrement count $I3_{C1}$, and the third instrument I3 operating in the third instrument's second actuator state $SIA_{32}$ is associated with the third instrument's second decrement count $I3_{C2}$.

It is noted that some surgical activities may involve use of an instrument such as an endoscope, for example, which is not worn down or degraded as result of its use. Also, some instruments such as instrument I2, are operable in only in a single routine actuator state, and are not operable in an alternative second actuator state, and therefore, is associated with only a single category of lifetime decrement. Moreover, in some embodiments, a lifetime decrement associated with an instrument actuator state is determined as a function of energy use over time during an instrument actuator state, and therefore the lifetime decrement for such instrument can be variable depending upon energy usage. In accordance with some embodiments, the more energy is used, the larger the lifetime decrement. For example, operation of an instrument at higher speed during an actuator state can result in use more energy than operation of the same instrument in the same actuator state at a lower speed.

Referring to the first row of the example information structure instance 1020$i$ of FIG. 13, for example, during activity A1, the first instrument I1 can be operated in the first instrument's first actuation state $SIA_{11}$, which results in decrementing the first instrument's remaining lifetime 668 by the first decrement count $I1_{C1}$. Alternatively, during activity A1, the first instrument I1 can be operated in the first instrument's second actuation state $SIA_{12}$, which results in decrementing the first instrument's remaining lifetime 668 by the second decrement count $I1_{C2}$.

Referring to the second row of the example information structure instance 1029$i$ of FIG. 13, for example, during surgical, the first activity A2 of the surgery can involve the second instrument I2 operated in the second instrument's first actuation state $SIA_{21}$, which results in decrementing the second instrument's remaining lifetime 668 by the first decrement count $I2_{C1}$. It is noted that there is no second instrument second actuation state in this example. Referring to the Nth row of the example information structure instance 1020$i$ of FIG. 13, for example, during the Nth activity AN, the third instrument I3 can be operated in the third instrument's first actuation state $SIA_{31}$, which results in decrementing the third instrument's remaining lifetime 668 by the first decrement count $I3_{C1}$. Alternatively, during activity AN, the third instrument I3 can be operated in the third instrument's second actuation state $SIA_{32}$, which results in decrementing the third instrument's remaining lifetime 668 by the second decrement count $I3_{C2}$.

Figure 14:
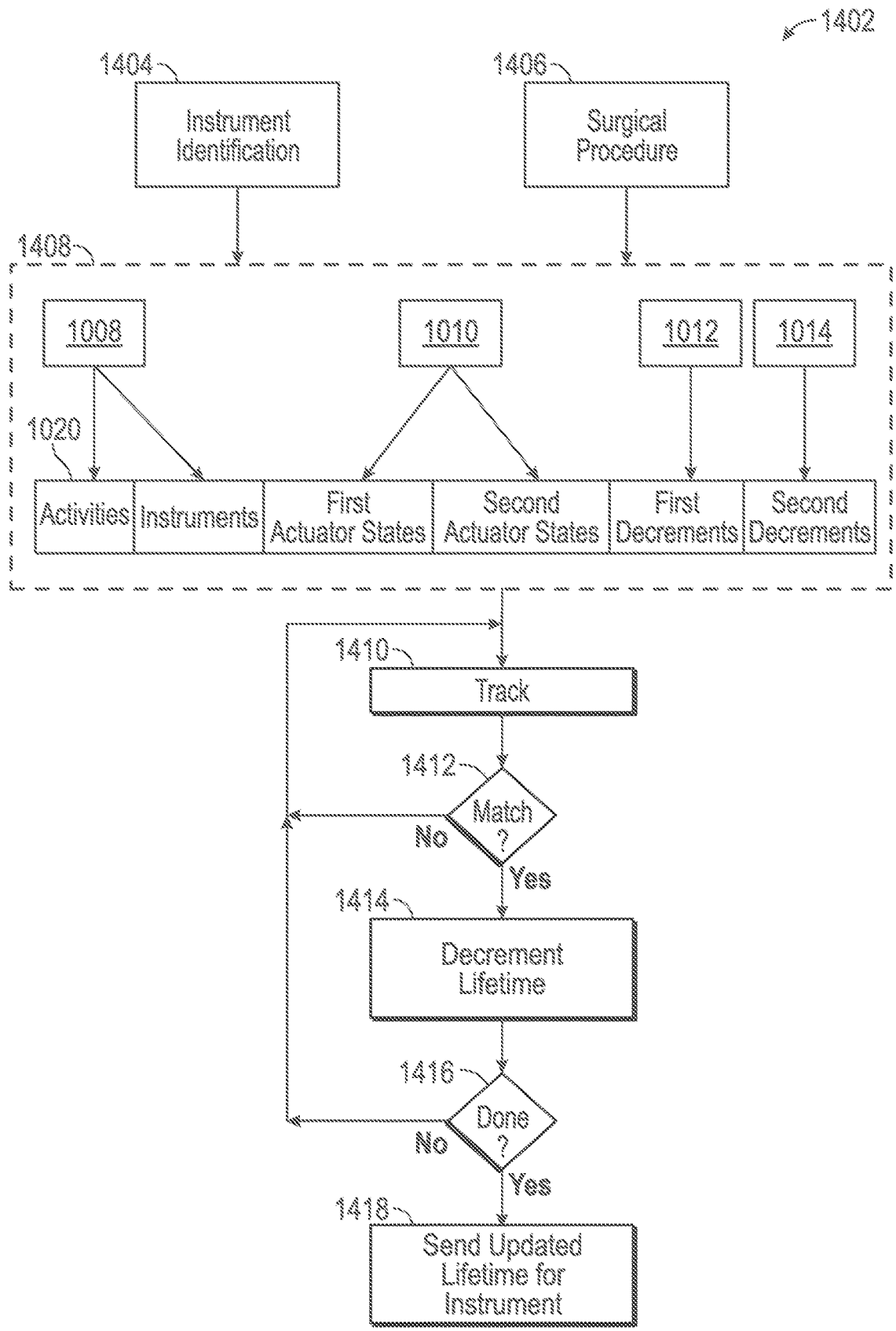
FIG. 14 is an illustrative flow diagram representing a process to configure processor to determine surgical instrument wear incurred during a surgical procedure in accordance with some embodiments.

FIG. 14 is an illustrative flow diagram representing a process 1402 to configure processor 58 to determine surgical instrument wear incurred during a surgical procedure in accordance with some embodiments. In block 1404, a surgical instrument identification is received at an input to a computer processing system associated with the electronics cart 56. The surgical instrument identification includes information to identify each individual instrument slated for use in a surgical procedure and corresponding remaining lifetime information identified instruments. In block 1406, an identification of a surgical procedure is received at an input of the computer processing system associated with the electronics cart 56. In block 1408, information included within the atlas 1002 within information structures 1008, 1010, 1012, 1014 and 1016 is used to produce an instance of the eighth information structure 1020 associating surgical activities with surgical instrument activity states and with surgical instrument lifetime decrements.

During performance of the identified surgical procedure, block 1410 tracks operational state of a surgical instrument actuator. In decision block 1412, a determination is made as to whether a current instrument actuator state matches an actuator state that is associated with a lifetime decrement for the instrument. In response to no match, control loops back to block 1410 and tracking continues. In response to a match, block 1414 decrements the identified instrument's remaining lifetime 668 based upon a lifetime decrement associated with the matching instrument actuator state. Decision block 1416 determines whether the surgical procedure is done. In response to a determination that the surgical procedure is not yet done, control next flows back to block 1410, which continues to track surgical instrument actuator state based upon other identified actuator state transition information, for example. In response to a determination that the surgical procedure is done, block 1418 uses the RFID reader 535 to read instrument identifier information 666 and corresponding remaining lifetime information 668 from the storage device 660 within the RFID 662 associated with the instrument and sends remaining lifetime information for the identified instrument to the inventory management system 860.

Assuming for example, that the process 1402 of FIG. 14 that the is performed for using the example information structure instance 1020i of FIG. 13, during performance of the surgical procedure, block 1410 tracks operational state of surgical instrument actuators for each of instruments I1, I2 and I3. In decision block 1412, a determination is made as to whether a current instrument actuator state of any one or more of the three surgical instrument actuators matches an actuator state that is associated with a lifetime decrement for the corresponding instrument. In response to no match, control loops back to block 1410 and tracking continues. In response to a match, block 1414 decrements an identified instrument's remaining lifetime 668 based upon a lifetime decrement associated with the matching instrument actuator state. For example, while tracking during surgical activity A1, the decision block 1412 determines whether a current actuator state of instrument I1 matches either of actuator state SIA11 or SAI21. In response to a match between the actuator state of I1 and $SIA_{11}$, a lifetime 668 for Il1 is decremented by $I1_{C1}$. In response to a match between the actuator state of I1 and $SIA_{21}$, a lifetime 668 for 11 is decremented by $I1_{C2}$. Control next flows to decision block 1416, which determines whether there are additional surgical states to be performed. In this example, surgical states A2 through AN are to be performed after surgical state A1. Accordingly, control flows back to block 1410, which continues to track surgical instrument actuator state during surgical activities A2 through AN based upon other identified actuator state transition information, for example. Upon completion of all surgical activities A1 through AN, block 1418 configures the processor to send an updated lifetime information for the identified instrument to the inventory management system 860.

Figure 15:
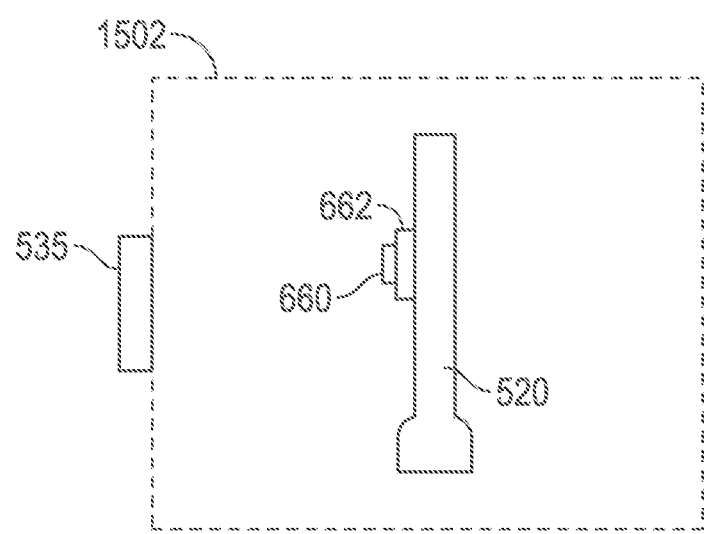
FIG. 15 is an illustrative drawing representing a sterilization chamber with a surgical instrument disposed inside it in accordance with some embodiments.

FIG. 15 is an illustrative drawing representing a sterilization chamber 1502 with a surgical instrument 520 disposed inside it in accordance with some embodiments. The surgical instrument is associated with an RFID device 662 and a storage device 660. In operation, following sterilization of an instrument prior to use of the instrument in a next surgery, the RFID reader 535 associated with the sterilization chamber 1502 reads instrument identifier information 666 and corresponding remaining lifetime information 668 from memory 660 for transmission to the inventory management system 860.

Although illustrative embodiments have been shown and described, a wide range of modification, change and substitution is contemplated in the foregoing disclosure and in some instances, some features of the embodiments may be employed without a corresponding use of other features. For example, in some embodiments, the processor 58 is coupled to a memory device such as storage device 1004 that includes an instruction set executable on the processor 58 to cause the processor 58 to perform operations. In some embodiments, the operations include providing in a first information structure in the memory device that associates a surgical instrument identifier with remaining useful lifetime of the identified surgical instrument. The operations further include tracking surgical instrument actuator state of the identified surgical instrument during performance of a surgical procedure. The operations further include reducing the associated remaining useful lifetime of the identified surgical instrument by a surgical instrument lifetime reduction amount in response to the tracked surgical instrument actuator state matching a surgical instrument wear-down actuation state during the performance of the surgical procedure.

One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A method for tracking use in a system of a surgical instrument comprising a radio frequency identification device (RFID), wherein the RFID includes a computer readable storage device that comprises a surgical instrument identifier and remaining lifetime information for the identified surgical instrument, the method comprising:
   attaching the surgical instrument to an instrument actuator on the system;
   adjusting the remaining useful lifetime information of the identified surgical instrument within the computer readable storage device to indicate a reduced useful lifetime, wherein adjusting the remaining useful lifetime information comprises:
   identifying a first surgical instrument actuator state for the surgical instrument during use of the system, and
   reducing the remaining useful lifetime information of the surgical instrument by a first surgical instrument lifetime reduction amount based upon the first surgical instrument actuator state
   identifying a second surgical instrument actuator state for the surgical instrument during the use of the system; and
   reducing the remaining useful lifetime status of the surgical instrument by a second surgical instrument lifetime reduction amount based upon the second surgical instrument actuator state.

2. The method of claim 1, further including:
   sending an indication of remaining useful lifetime over a network to an inventory management system.

3. The method of claim 1 further including:
   providing in an information structure in a computer readable storage device an association between a surgical instrument wear-down actuation state and a surgical instrument lifetime reduction amount.

4. The method of claim 3,
   wherein providing in the information structure in the computer readable storage device an association includes, providing a first association between a first wear-down actuation state and a first lifetime reduction amount and providing a second association between a second wear-down first actuation state and a second lifetime reduction amount.

5. A surgical system that includes a surgical instrument and a surgical instrument actuator comprising:
   a processor;
   a memory device holding an instruction set executable on the processor to cause the processor to perform operations comprising:

providing an information structure in a memory device that provides a first association between a first surgical instrument wear-down actuation state and a first useful lifetime reduction amount and that provides a second association between a second surgical instrument wear-down actuation state and a second useful lifetime reduction amount;

tracking surgical instrument actuator state of the identified surgical instrument during performance of a surgical procedure;

determining whether during the performance the instrument actuator state matches a first surgical instrument wear-down actuator state;

in response to determining that the instrument actuator state matches the first surgical instrument wear-down actuator state during the performance, adjusting first associated remaining useful lifetime information of the identified surgical instrument based upon a first useful lifetime reduction amount;

determining whether during the performance the instrument actuator state matches a second surgical instrument wear-down actuator state; and in response to determining that the instrument actuator state matches the second surgical instrument wear-down actuator state during the performance, adjusting second associated remaining useful lifetime information of the identified surgical instrument based upon the second useful lifetime reduction amount.

6. The system of claim 5, the instruction set causing the processor to perform further operations including:

associating a tracking device with the identified surgical instrument; and providing the information structure in a computer readable storage device in the tracking device.

7. The system of claim 5, further including:

sending an indication of the remaining lifetime over a network to an inventory management system.

8. A method for use with a system that includes a surgical, comprising:

providing in an information structure in a memory device that provides a first association between a first surgical instrument wear-down actuation state and a first useful lifetime reduction amount and that provides a second association between a second surgical instrument wear-down actuation state and a second useful lifetime reduction amount;

attaching the surgical instrument to an instrument actuator on the system; and adjusting a remaining useful lifetime information of the identified surgical instrument within the computer readable storage device to indicate a reduced useful lifetime, wherein adjusting the remaining useful lifetime information comprises:

determining whether during the use of the surgical instrument, a surgical instrument actuation state matches the first surgical instrument wear-down actuation state;

in response to determining that a surgical instrument actuation state matches the first surgical instrument wear-down actuation state during the use, reducing the remaining useful lifetime information of the surgical instrument by the first useful lifetime reduction amount;

determining whether during the use of the surgical instrument, a surgical instrument actuation state matches the second surgical instrument wear-down actuation state; and in response to determining that a surgical instrument actuation state matches the second surgical instrument wear-down actuation state during the use, reducing the remaining useful lifetime information of the surgical instrument by the second useful lifetime reduction amount.

9. The method of claim 8, further including:

sending an indication of the remaining lifetime information over a network to an inventory management system.

10. A surgical method for use with a teleoperated surgical system that includes a surgical instrument and a surgical instrument actuator, comprising:

associating a radio frequency identification device (RFID) with the surgical instrument;

providing in the RFID information structure in a computer readable storage device that provides a first association between a first surgical instrument wear-down actuation state and a first useful lifetime reduction amount and that provides a second association between a second surgical instrument wear-down actuation state and a second useful lifetime reduction amount attaching the surgical instrument with the associated RFID to an instrument carriage that includes actuator outputs;

actuating the surgical instrument using the actuator outputs to change a surgical instrument actuator state during a surgical procedure;

tracking surgical instrument actuator state of the identified surgical instrument during performance of a surgical procedure;

actuating the surgical instrument using the actuator outputs to change a surgical instrument actuator state during a surgical procedure;

determining whether during the use of the surgical instrument, a surgical instrument actuation state matches the first surgical instrument wear-down actuation state;

in response to determining that a surgical instrument actuation state matches the first surgical instrument wear-down actuation state during the use, reducing the remaining useful lifetime information of the surgical instrument by the first useful lifetime reduction amount;

determining whether during the use of the surgical instrument, a surgical instrument actuation state matches the second surgical instrument wear-down actuation state; and in response to determining that a surgical instrument actuation state matches the second surgical instrument wear-down actuation state during the use, reducing the remaining useful lifetime information of the surgical instrument by the second useful lifetime reduction amount;

reading the reduced useful lifetime from the computer readable storage device by an RFID reader; and sending an indication of the remaining lifetime over a network to an inventory management system.

* * * * *

UNITED STATES PATENT AND TRADEMARK OFFICE
CERTIFICATE OF CORRECTION

| | | |
|---|---|---|
| PATENT NO. | : 11,311,347 B2 | Page 1 of 1 |
| APPLICATION NO. | : 16/349208 | |
| DATED | : April 26, 2022 | |
| INVENTOR(S) | : Hingwe et al. | |

It is certified that error appears in the above-identified patent and that said Letters Patent is hereby corrected as shown below:

In the Claims

In Column 18, Line 38, in Claim 1, after "state", insert --;--

In Column 19, Line 29, in Claim 6, before "system", insert --surgical--

In Column 19, Line 35, in Claim 7, before "system", insert --surgical--

In Column 20, Line 26, in Claim 10, after "amount", insert --;--

Signed and Sealed this
Twenty-fifth Day of October, 2022

Katherine Kelly Vidal
*Director of the United States Patent and Trademark Office*